Feb. 13, 1951 P. J. HOWARD Plant Pat. 1,004
ROSE PLANT
Filed Nov. 4, 1949
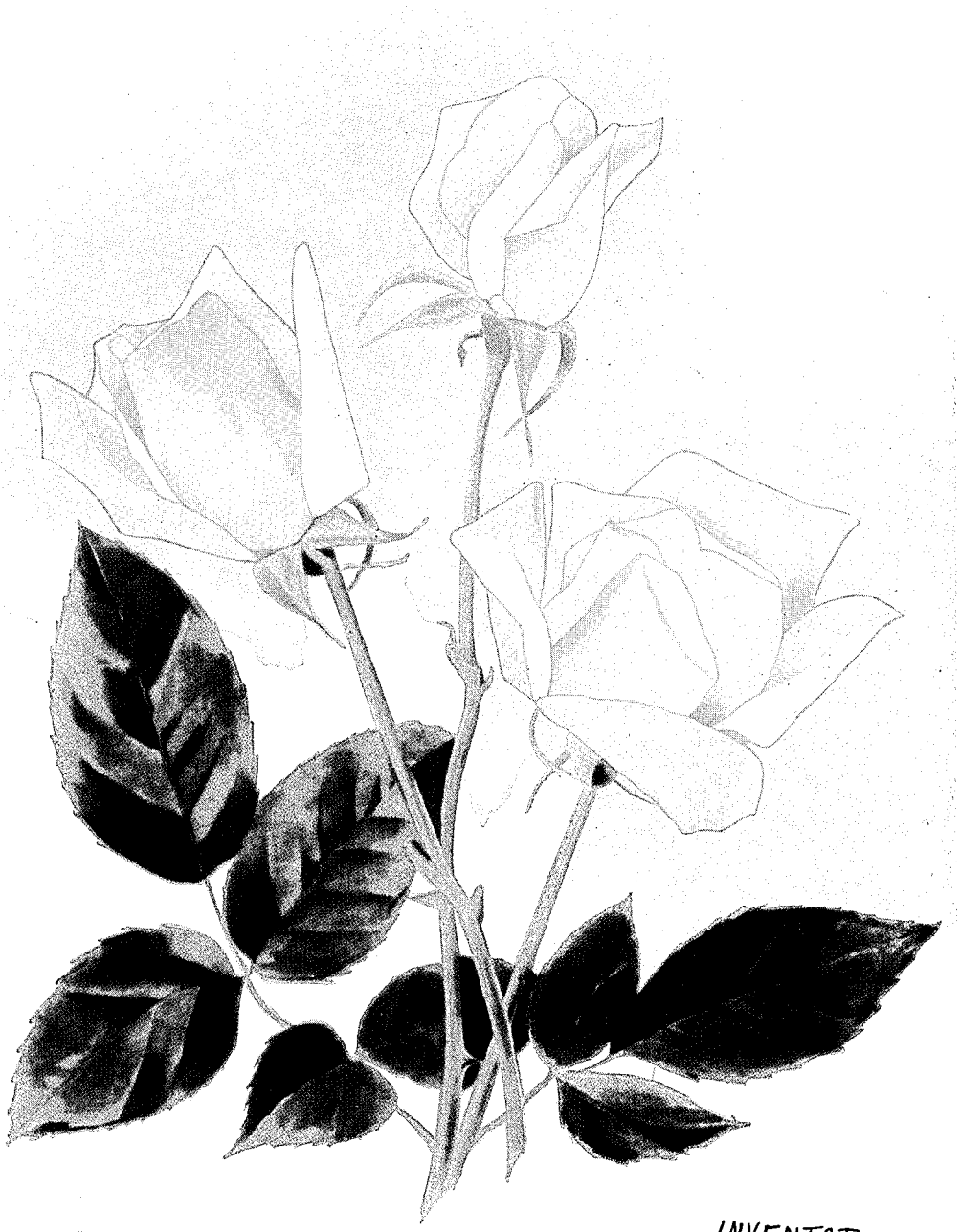
INVENTOR
Paul J Howard
By Orville M. Kile
Plant Pat. Agt.

Patented Feb. 13, 1951

Plant Pat. 1,004

UNITED STATES PATENT OFFICE 1,004

ROSE PLANT

Paul J. Howard, Los Angeles, Calif., assignor to Paul J. Howard California Flowerland, Los Angeles, Calif., a corporation Application November 4, 1949, Serial No. 125,432

1 Claim. (Cl. 47—61)

My present invention relates to a new and distinct variety of hybrid tea rose plant, the result of an effort to produce an improvement in white roses. It resulted from a cross between the varieties Capt. Thomas (Plant Patent 393) and Eternal Youth (Plant Patent 332), made by me at my gardens in Los Angeles, California.

Most outstanding among its characteristics are its intense fragrance, vigorous growth and production of leathery foliage in abundance, unlike other white roses. Also it is a free and continuous bloomer, bearing its large flowers both singly and in clusters of three or four. Its flowers vary greatly in form in different seasons and locations and the field-grown flowers differ greatly from those grown under glass. Yet all have the outstanding characteristics mentioned.

The accompanying illustrations show typical greenhouse-grown specimens of the blooms of my new variety.

My new variety has been asexually reproduced by budding in my Southern California nurseries and in several other nurseries of the same general location, and its characteristics appear to be permanent.

Following is a detailed description of my new rose, in which color terminology refers to Ridgway's Color Standards and Nomenclature and other color terms without plate references indicating the ordinary dictionary meaning.

*The plant*

Growth: Vigorous and strong.

Form: Tall, upright bush, averaging 4½ to 5 feet in height.

Blooming habit: Free and continuous. Blooms are borne both singly and in clusters of 3 or 4.

Stems: Medium to heavy. Strong and upright. Approximately Oil Green (Pl. V), with russet overlay on the portion exposed to sun.

Thorns: Many large thorns, sharp, irregularly placed, slightly downward-hooked and usually reddish-tinged. Many small prickles are irregularly placed on peduncle, and sharp spines on under side of rachis and between the thorns on the stem.

Foliage:

*Quantity.*—Abundant.

*Leaflets.*—3 to 7.

*Size.*—Large. Terminal leaflet is about 3 inches long by 1½ inches wide.

*Shape.*—Elliptical with rounded base and acute apex. Edge finely serrated and slightly undulate.

*Texture.*—Heavy and leathery.

*Color.*—Approximately Yew Green (Pl. XXXI).

*Stipules.*—Very narrow and clinging.

*Rachis.*—Slender. Upper side grooved; lower side thorny.

*The flower*

Bud:

*Size.*—Medium.

*Form.*—Long and slender; pointed. Bud of outdoor-grown plant is broader than that of plants grown under glass.

*Color.*—On the summer flowers practically all of the color visible when the calyx breaks is from Rose Color (Pl. XII) to Old Rose (Pl. XIII). As it begins to open, the principal portion is creamy white or approximately Naphthalene Yellow (Pl. XVI), with Pale Chalcedony Yellow (Pl. XVII) at the base. The buds of the spring flowers do not show any red.

*Sepals.*—Short and fairly simple; reflex early; heavy substance.

*Peduncle.*—Short and spiny; strong and rigid; color slightly lighter than stems.

Bloom:

*Size.*—Large, measuring 4 to 6 inches in diameter when fully expanded.

*Form.*—High centered, finally opening into loose cupshape revealing the numerous pistils and stamens. The main crop of blossoms comes in the spring and the form of them is almost exactly like that of Peace (Plant Patent No. 591).

*Behavior of petals.*—Drop off cleanly.

*Substance of petals.*—Medium.

*Size of petals.*—Average is 2 to 2½ inches in length and about the same in width.

*Shape of petals.*—Outer petals orbicular and considerably cupped. Edges only slightly recurved in spring blossoms. Inner petals straighter and narrower.

*Petalage.*—Average, 38 petals.

*Color.*—Grown outdoors, the flowers are creamy white with slight greenish-yellow tinge approximately Pale Chalcedony Yellow (Plate XVII), and as the flower opens the inner petals become a slightly deeper yellow approximately Naphthalene Yellow (Plate XVI). When grown under glass, the flowers are neary pure white. The blooms vary greatly according to the season and the conditions under which they are grown.

*Fragrance.*—Very rich and intense.

*Longevity.*—Good both as cut flower and on the bush.

Reproductive organs:

*Pistils.*—Many; bunched; partially enclosed in calyx. *Styles* white, even in length. *Stigmas* slightly pink-tinged.

*Stamens.*—Many; surrounding pistils; emerging from edge of calyx to approximately the same height as pistils—the whole constituting a cushion effect.

Having thus disclosed my invention, I claim:

The new and distinct variety of hybrid tea rose plant, substantially as herein shown and described, characterized particularly by the combination of tall, vigorous growth; its free and continuous production of flowers both singly and in clusters; its abundant, large leathery leaves; the unusual and varied form and essentially white color of its flowers; its rich fragrance unusual in white roses; and its adaptability to both garden and greenhouse culture.

PAUL J. HOWARD.

No references cited.